United States Patent [19]

Carter, Jr. et al.

[11] 4,340,825
[45] Jul. 20, 1982

[54] TOUCH DETECTOR FOR ELECTRON APPLICATOR

[75] Inventors: James C. Carter, Jr., San Jose; Stanley Mansfield, Santa Clara, both of Calif.

[73] Assignee: Varian Associates, Inc., Palo Alto, Calif.

[21] Appl. No.: 191,109

[22] Filed: Sep. 26, 1980

[51] Int. Cl.³ .......................................... G01N 23/00
[52] U.S. Cl. .................................. 307/116; 200/61.43
[58] Field of Search ............................. 307/116, 119; 200/61.43, 61.44, 166, 85 R, 52 R, 61.93

[56] References Cited

U.S. PATENT DOCUMENTS

| | | | |
|---|---|---|---|
| 1,240,147 | 9/1917 | Johnston | 200/61.57 |
| 2,946,869 | 7/1980 | Parks et al. | 200/61.57 |
| 3,053,948 | 9/1962 | Figenshaw | 200/61.42 |
| 3,325,611 | 6/1967 | Gourley et al. | 200/61.39 |
| 3,330,923 | 7/1967 | Brockmeyer et al. | 200/61.43 |
| 3,443,658 | 5/1969 | Culp | 200/61.44 X |
| 3,902,070 | 8/1975 | Amor et al. | 250/525 |
| 4,045,631 | 8/1977 | Dann | 200/61.43 |
| 4,088,856 | 5/1978 | Tebben | 200/52 R |

Primary Examiner—Michael L. Gellner
Assistant Examiner—James L. Dwyer
Attorney, Agent, or Firm—Stanley Z. Cole; Keiichi Nishimura

[57] ABSTRACT

The present invention provides a touch detector for preventing collision involving an electron therapy applicator. A sensor is suspended from a cable wrapped on a system of pulley wheels and attached to a spring. By adjusting the configuration and tension of the cable properly with respect to the weight of the sensor, the detector sensitivity can be made reasonably independent of the direction of the detected force as well as the position of the apparatus.

10 Claims, 6 Drawing Figures

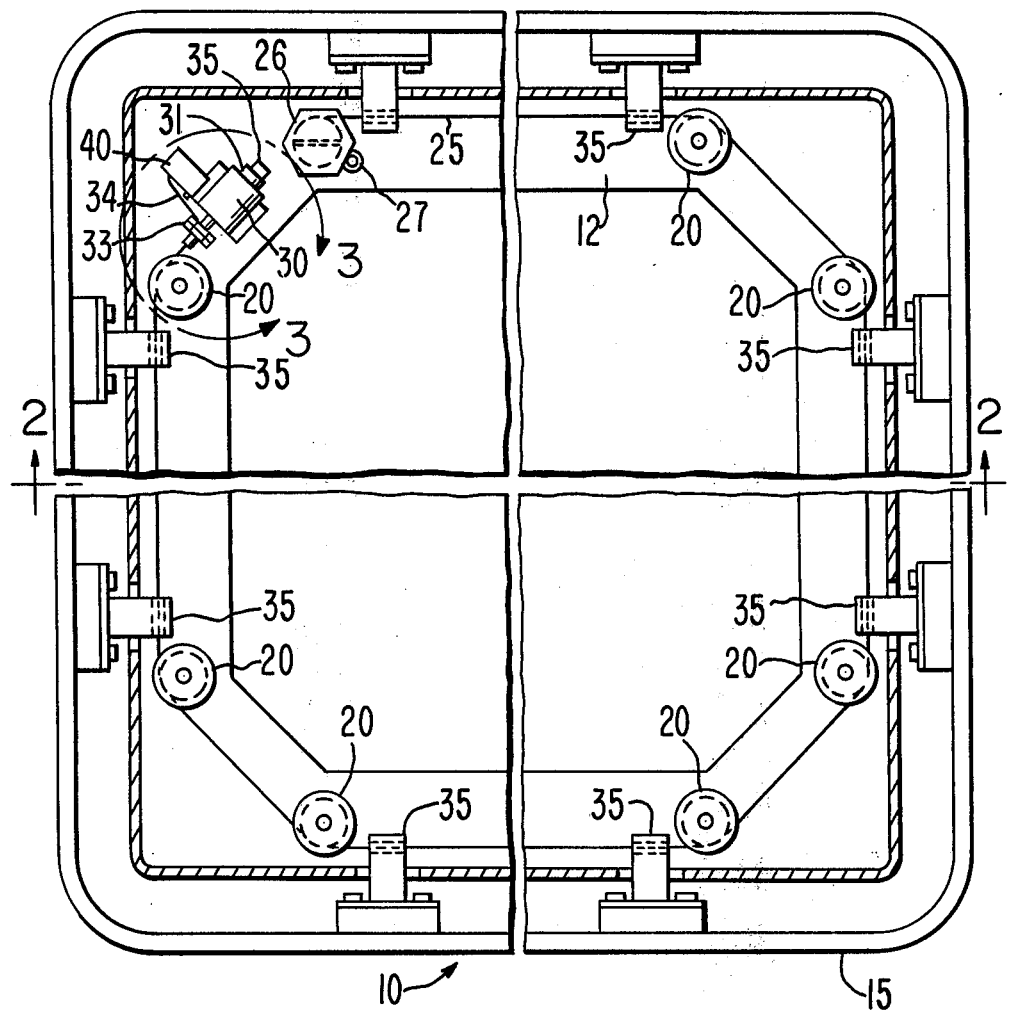
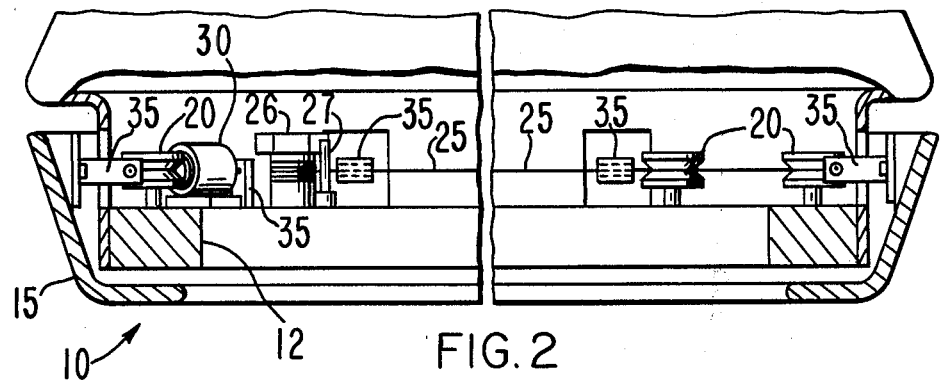

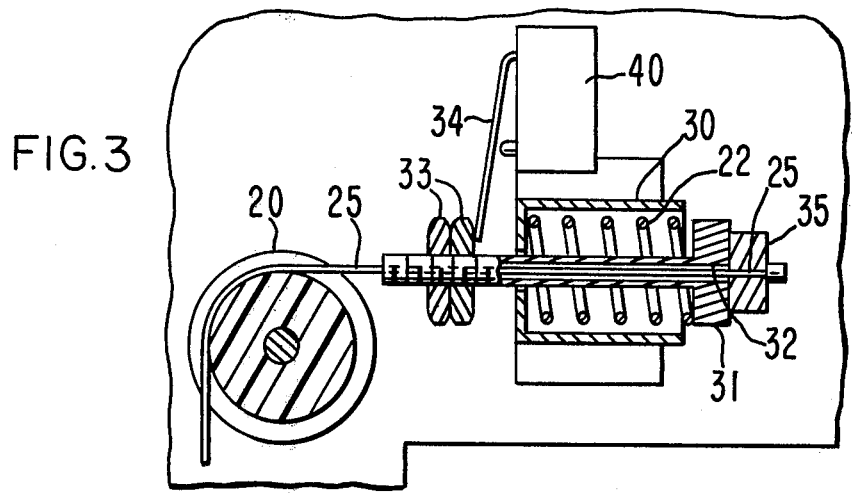
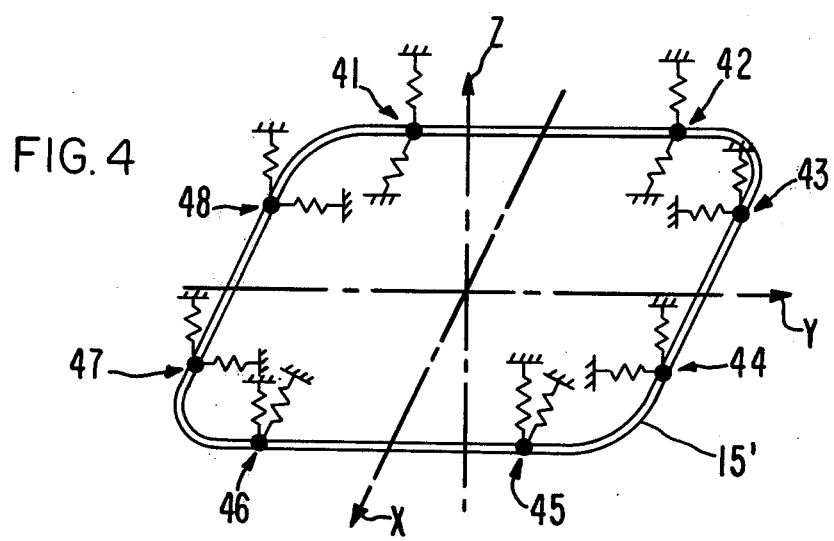
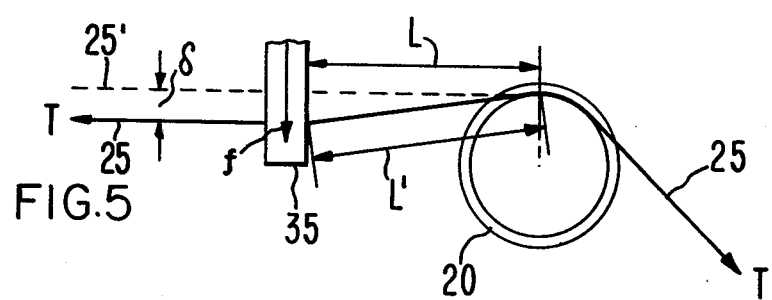

MODE 1  15  $F_X$

MODE 2  15  $F_Y$

15  MODE 3  $F_Z$

15  $F_Z$  MODE 4  $F_Z$

TOUCH DETECTOR FOR ELECTRON APPLICATOR

DESCRIPTION

1. Field of the Invention

The present invention relates to a touch detector for sensing collision involving a movable apparatus such as an electron therapy applicator, and more particularly to such a detector of which the sensitivity is independent of the position and attitude, and which will respond effectively against external forces applied in a wide range of directions.

2. Background of the Invention

A touch detector, or a safety device for detecting collision and preventing damage or injury by sensing obstructions, is an essential feature of many movable apparatus. This is particularly the case with an electron therapy applicator because such an apparatus is typically operated at a nominal distance of about 5 cm from the patient for normal treatment and it is desirable to prevent the patient from being disturbed by significant contact from the end of the applicator.

Although there have been proposed many types of touch detecting and/or collision-preventing devices, most of them are not readily applicable to a radiation therapy apparatus for a variety of reasons. Firstly, a therapy apparatus must be able to operate while taking different positions and attitudes. It is hence desirable that the sensitivity of the touch detector therefor be reasonably independent of the direction in which it is set up. Secondly, such an apparatus is usually more freely movable and rotatable than, for example, a sliding door against which collisions need be considered only from one direction. Thirdly, a radiation therapy machine must have an opening for a beam to pass through. Such an opening must face the direction of the patient under treatment and this is exactly the direction along which the apparatus is most likely to have accidental collisions. Most of the presently available touch detectors which have been developed for other types of apparatus cannot be adopted to a radiation therapy apparatus because of their basic structural requirements.

Attempts in the past to develop a touch detector for a radiation therapy apparatus have resulted, for example, in a device designed to "collapse" away in the event of a collision rather than to actually stop the motorized motion. Such a system not only fails to provide a full protection to the patient but also is disadvantageous in that the full weight of the suspended portion must be supported at a plane other than at its center of gravity. The weight to be thus supported can be large enough to significantly impair the sensitivity of the system.

SUMMARY OF THE INVENTION

It is an object of the present invention to provide a touch detector for a radiation therapy apparatus such as an electron applicator.

It is another object of this invention to provide a touch detector which is sensitive to forces applied in various directions.

It is still another object of this invention to provide a touch detector with sensitivity which is both easily adjustable and reasonably independent of the direction of the applied force and the attitude of the detector.

These and still further objects of this invention will become apparent to those skilled in the art from an analysis of the following description of a specific embodiment of the invention.

BRIEF DESCRIPTION OF THE DRAWINGS

FIG. 1 is a plan view of apparatus embodying the present invention.

FIG. 2 is a cross-sectional view taken along line 2—2 of FIG. 1.

FIG. 3 is an enlarged sectional view of a portion of the apparatus of FIG. 1 delineated by line 3—3.

FIG. 4 shows an equivalent system of springs for illustrating the dynamics of the sensor of FIGS. 1 and 2.

FIG. 5 shows the relationship between a linear displacement of a segment of the cable and its contribution to the over-all travel of the spring regarding the detector of FIGS. 1 and 2.

DETAILED DESCRIPTION OF THE INVENTION

Figure 6A:
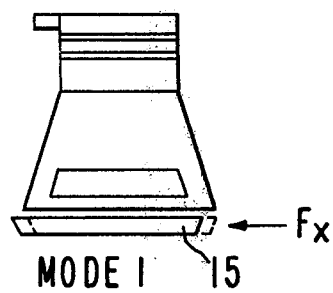
FIG. 6 shows the four basic modes of sensor displacement regarding the detector of FIGS. 1 and 2.
Figure 6B:
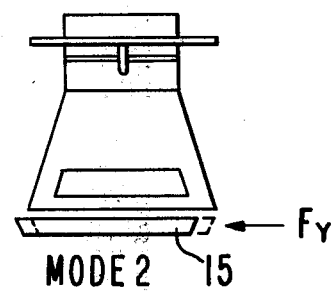
Figure 6C:
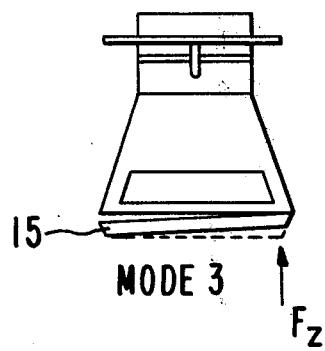
Figure 6D:
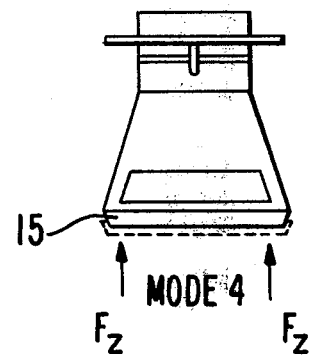

According to one embodiment of the present invention shown in FIGS. 1, 2 and 3, the basic components of touch detector 10 are a frame 12 and a sensor 15. Frame 12 is rigidly affixed to an apparatus, or a part of an apparatus, (not shown) which is to be protected against accidental collisions during its motorized operation. Such an apparatus, or a part of an apparatus, is generally capable not only of linear movements but also of assuming various positions, or attitudes, over a considerably large range. Sensor 15, on the other hand, is displaceable with respect to frame 12 and is formed as a square-like tray with the four corners smoothly rounded off for safety. Sensor 15 is large enough to and does completely cover the surface which is to be protected and on which frame 12 is affixed. If the apparatus to be protected is a radiation therapy apparatus such as an electron applicator having an opening for a beam, both frame 12 and sensor 15 must be provided with an aperture. The apertures must be large enough and so positioned to allow an unobstructed passage of the beam from the apparatus, or they may be designed to serve the function of defining the size and shape of the beam which passes therethrough.

Mounted on frame 12 are seven pulley wheels 20, a compression spring 22 of the ordinary spiral type and a capistan 26 for cable pre-tensioning. Spring 22 is positioned inside guide barrel 30 so that its one-dimensional motions are restricted along its own direction. Affixed to the free-moving end of spring 22 so as to move therewith is an end screw 31 having a hole 32 for cable 25 to pass through. Affixed to one end of cable 25 is a termination piece 29 which is sufficiently large with respect to the hole 32 and hence unable to pass therethrough. Cable 25 passes over the seven pulley wheels 20 and the other end thereof (non-terminated end) penetrates a hole in capstan 26. The length of and hence the tension inside cable 25 can be adjusted to a pre-selected value by using capistan 26 to bring termination piece 35 into contact with end screw 31 and by working against compression spring 22. Capstan 26 and the seven pulley wheels 20 are so positioned on frame 12 that the pre-tensioned cable 25 will assume an octagonal shape and the motion of cable 25 due to the tensile force therein can be transmitted to the spring 22 directly. Capstan 26 has a hexagonal head and is held in position by means of a spring-loaded pin 27.

Affixed to the inside surface of the tray-shaped sensor 15 are eight cable bosses 35 by means of which sensor 15 is suspended from cable 25. They may be of any simple structure but since they are expected also to perform the function of accurately transmitting to cable 25 and eventually to spring 22 the effect of any external force which may be sensed by sensor 15, they may be provided with a hole through which cable 25 can pass. The holes must be so positioned that the octagonal shape described by cable 25 will not be affected in the absence of external force applied on sensor 15. Furthermore, it is preferable that cable bosses 35 be symmetrically positioned with respect to the octagon so that the weight of sensor 15 is uniformly distributed among the segments of cable 25 stretched between two adjacent pulley wheels.

Touch detector 10 is further provided with a switch 40 for opening a circuit (not shown) when sensor 15 sends a signal that a collision has occurred. A pair of jam nuts 33 are attached to end screw 31, and switch activator arm 34 made of a simple metal piece abuts one of the jam nuts 33. The jam nuts are so adjusted that the circuit will be opened whenever sensor 15 is deflected relative to frame 12 sufficiently to cause a displacement of spring 22 by a distance greater than a predetermined threshold value. Such circuit is generally for controlling the motorized motion of the apparatus to be protected but it must also be for stopping its entire operation such as stopping the beam if the apparatus in question is a radiation therapy apparatus such as an electron applicator.

The dynamics of sensor 15 illustrated in FIGS. 1 and 2 can be examined most conveniently by considering a square-shaped system 15' representing sensor 15 suspended by eight sets of two springs arranged three-dimensional as shown in FIG. 4. Eight points 41 through 48 represent the positions where sensor 15 is suspended from cable 25 by means of cable bosses 35. This model is adequate because each segment of cable 25 can exert a force to the cable bosses in contact only in perpendicular directions, acting in each of these perpendicular directions as a linear spring within a certain limit of travel. For convenience a set of cartesian coordinates is defined as shown with the x- and y-axes lying respectively parallel to each of two mutually adjacent sides of square system 15' and the z-axis being perpendicular to the plane thereof.

The effect on spring 22 of an external force acting on sensor 15 is now considered with the help of FIG. 5 which illustrates a simple linear displacement $\delta$ of cable boss 35 along the direction of the boss. Any displacement in a direction perpendicular to the portion of cable 25 supporting the boss can be discussed similarly. Dotted line 25' indicates the original position of cable 25 while solid line 25 indicates its displaced position. If the distance between cable boss 35 and the pulley wheel 20 nearest it is denoted by L before the displacement and by L' after the displacement, distance d defined by L'−L, or $\sqrt{\delta^2+L^2}-L$ is that portion of the travel of spring 25 due to the displacement of this particular cable boss. A simple vector addition shows that the force f exerted on cable boss 35 by cable 25 in the displaced state shown in FIG. 5 is given by $T(\delta/L)$ where T is the tension inside the cable 25 and may be considered independent of the external force if, as in most practical embodiments, the maximum allowable value of $\delta$ is much smaller than L.

With reference to the coordinate system introduced above, it is now possible to consider the following four basic displacement modes of square system 15'. They are illustrated in FIG. 6 wherein square system 15' is illustrated as a tray-shaped sensor 15 as in FIG. 2 and arrows therein marked $F_j$ (j=x,y,z) respectively represent a force in the direction of the axis indicated by the subscript. Thus, FIG. 6(a) is a view of square 15' of FIG. 4 and the apparatus to be protected against collision (not shown in previous figures) as seen in the direction of the negative y-axis, and FIGS. 6(b), (c) and (d) are views of the same as seen in the direction of the negative x-axis. The four basic displacement modes are a displacement along the x-axis (Mode 1), a displacement along the y-axis (Mode 2), equal displacements of points 43 and 44 along the z-axis, and a uniform displacement of the entire sensor 15 (or system 15') along the z-axis (Mode 4). Other modes can be constructed by combining these basic modes, e.g., Mode 5 by combining Modes 1 and 2 (i.e., any linear displacement in the x-y plane), Mode 6 combining Modes 1 and 3 or Modes 2 and 3, Mode 7 by combining Modes 1, 2 and 3, Mode 8 by combining Modes 1 and 4 or Modes 2 and 4, and Mode 9 by combining Modes 1, 2 and 4. For each mode of displacement, the total movement of cable 25 (or the stretch of spring 22) can be expressed in terms of d, or in terms of $\delta$, by examining which ones of the $2\times 8=16$ springs in FIG. 4 are stretched or compressed. For Mode 1, for example, the horizontal springs at points 41, 42, 45 and 46 alone are compressed or stretched, and hence the total movement D=4d for Mode 1. Similarly, D=4d for Modes 2 and 3, D=8d for Modes 4, 5 and 6, D=12d for Modes 7 and 8, and D=16d for Mode 9. For a typical embodiment whereby L=0.75, T=10 lbs. and the maximum value of $\delta$=0.12 (distances in inches), it is seen that D=0.038 for Mode 1. This is well over the differential travel of several stock microswitches. In the case of Mode 9 where the maximum travel occurs, D=0.152 and this must be allowed for in the mechanism.

The apparatus to which touch detector 10 is attached is routinely moved in all directions but it is desirable that the sensitivity of detector 10 be independent of its orientation, or attitude. If sensor 15 weights 8 oz., however, D=0.00468 at the 90° position, or when the plane of system 15' is vertical (Mode 1 or 2) while D=0.00234 at the 0° position, or when the plane of system 15' is horizontal (Mode 4). At the intermediate positions, the value of D falls between the above two values. Therefore, the maximum change in travel due to the rotation of the apparatus is 0.0023 which is very nearly negligible as switch 40 can be set to ignore such small travels. Likewise, the maximum travel force for lateral motion is computed to be F=6.4 lb. (Mode 1). This leads to the over-all conclusion that touch detector 10 is not sensitive to changes in position or attitude, and yet it is sensitive to any exterior contact beyond a pre-set value in the neighborhood of 6 lbs. Because this system represents a momentary switch, a resettable relay will be required and a reset switch thus placed will allow easy system reset in the event of an accidental "trip." Since the switch operates by opening a circuit, it operates in a fail safe mode. The only mechanical failure that is not thus protected would be a failure in the cable or pulley system, but such a failure would affect the suspension of sensor 15 and hence would be readily detectable by the operator.

This invention has been described above in terms of a particular embodiment. The above description, however, is to be considered as illustrative rather than limiting. For example, it is to be appreciated that the numbers of pulleys and cable bosses as well as the geometrical figures to be described by the cable may be suitably modified, depending upon the size and shape of the sensor which, in turn, may depend upon the geometry of the apparatus to be protected. It is further to be appreciated that pulleys 20 may be replaced by any suitable pivotal guide arms or fixed guides without the necessity of wheels. The scope of the invention is defined by the following claims.

We claim:

1. A touch detector with sensitivity substantially independent of the orientation of said detector and the direction of activating force comprising:
    a frame,
    a sensor,
    an elastic member affixed to said frame and having a movable free end,
    a cable with one end affixed to said frame and the other end affixed to said free end of said elastic member, and,
    a guiding means supported by said frame for maintaining said cable in a predetermined tensioned position with respect to said frame in the absence of any external force on said sensor,
    said sensor being supported by said cable and movable relative to said frame in two orthogonal planes so that an external force applied on said sensor in either of said two orthogonal planes has the effect of deforming said elastic member by displacing said cable from said predetermined tensioned position.

2. The touch detector of claim 1 further comprising an electrical switching means adapted to be activated by distortion of said cable in response to displacement of said sensor by contact with an external surface.

3. A touch detector of claim 2 wherein said electrical switching means is cooperatively associated with said elastic member such that said electrical switching means is activated when said elastic member undergoes a deformation of a predetermined magnitude.

4. The touch detector of claim 3 wherein the weight of said sensor, the elastic constant of said elastic means, and the movement of said elastic means required for activation of said electrical switching means are so related that said electrical switching means is not activated by gravitational force acting on said sensor regardless of the orientation of said touch detector.

5. The touch detector of claim 1 wherein said guiding means comprises a plurality of pulleys mounted on said frame.

6. The touch detector of claim 5 wherein said pulleys are arranged in a polygonal formation.

7. The touch detector of claim 1 wherein said elastic member is a spring.

8. The touch detector of claim 1 wherein said frame and said sensor have a central aperture and wherein said frame is rigidly affixed to an electron applicator.

9. The touch detector of claim 1 wherein said frame and sensor are annular, and said sensor has a side portion spaced around said frame and an inturned end portion spaced from and projecting across a portion of the end of said frame.

10. A touch detector comprising:
    a frame;
    a sensor;
    means for supporting said sensor on said frame for movement of said sensor in all directions relative to said frame; said supporting means comprising a cable, guide means for said cable and elastic means for maintaining said cable under tension along said guide means in a predetermined configuration in the absence of any external force on said sensor; said support means being so arranged that said cable provides the sole support for said sensor; and
    switch means operatively arranged to be activated by predetermined distortion of said cable from said predetermined configuration;
    the weight of said sensor, the strength of said elastic means and the construction of said switch means being such that the gravitational force on said sensor in any orientation of said detector is insufficient to cause activation of said switch means.

* * * * *